United States Patent [19]

Wong et al.

[11] Patent Number: 4,612,008

[45] Date of Patent: Sep. 16, 1986

[54] OSMOTIC DEVICE WITH DUAL THERMODYNAMIC ACTIVITY

[75] Inventors: Patrick S. L. Wong, Hayward; Brian Barclay, Sunnyvale; Joseph C. Deters, Mt. View; Felix Theeuwes, Los Altos, all of Calif.

[73] Assignee: Alza Corporation, Palo Alto, Calif.

[21] Appl. No.: 685,092

[22] Filed: Dec. 21, 1984

Related U.S. Application Data

[63] Continuation-in-part of Ser. No. 493,760, May 11, 1983, abandoned.

[51] Int. Cl.[4] ..................... A61M 7/00; A61M 31/00
[52] U.S. Cl. .................................. 604/892; 604/890; 604/891; 604/285
[58] Field of Search ................ 604/890, 285, 892, 891

[56] References Cited

U.S. PATENT DOCUMENTS

| | | | |
|---|---|---|---|
| 4,186,184 | 1/1980 | Zaffaroni | 604/892 |
| 4,210,139 | 6/1980 | Higuchi | 604/892 |
| 4,298,003 | 11/1981 | Theeuwes et al. | 604/892 |
| 4,320,759 | 3/1982 | Theeuwes | 604/892 |
| 4,350,271 | 9/1982 | Eckenhoff | 604/892 |

Primary Examiner—John Kight
Assistant Examiner—M. L. Moore
Attorney, Agent, or Firm—Paul L. Sabatine; Edward L. Mandell; Steven F. Stone

[57] ABSTRACT

An osmotic system is disclosed comprising a wall formed in at least a part of a semipermeable material that surrounds a compartment. The compartment contains a first osmotic composition comprising a beneficial agent, and a second and different osmotic composition. A passageway in the wall connects the first composition with the exterior of the system.

27 Claims, 14 Drawing Figures

4,612,008

OSMOTIC DEVICE WITH DUAL THERMODYNAMIC ACTIVITY

CROSS-REFERENCE TO RELATED PATENT APPLICATIONS

This application is a continuation-in-part of U.S. Pat. Appln. Ser. No. 493,760 filed on May 11, 1983, now abandoned, which application is incorporated herein by reference and benefit is claimed of its filing date. This application is copending with the applicants' application ARC 1019 CIP-2 identified as U.S. Pat. Appln. 685,687 filed Dec. 24, 1984. These patent applications are assigned to the ALZA Corporation of Palo Alto, California.

FIELD OF THE INVENTION

This invention pertains to both a novel and unique delivery system. More particularly, the invention relates to an osmotic device comprising a wall formed in at least a part of a semipermeable material that surrounds a compartment comprising: (1) a first osmotic composition comprising a beneficial agent, an osmagent and an osmopolymer, said composition in contacting arrangement with (2) a second osmotic composition comprising an osmagent and an osmopolymer. A passageway through the wall connects the exterior of the osmotic device with the first osmotic composition containing the beneficial agent for delivering the first composition from the osmotic device. The osmotic device is useful for delivering beneficial agents that because of their solubilities are difficult to deliver in a known amount at a controlled rate from an osmotic dispensing system.

BACKGROUND OF THE INVENTION

Since the beginning of antiquity, both pharmacy and medicine have sought a delivery system for administering a beneficial drug. The first written reference to a delivery system is to the Eber Papyrus, written about 1552 B.C. The Eber papyrus mentions delivery systems made as dosage forms such as anal suppositories, vaginal pessaries, ointments, oral pill formulations, and other dosage preparations. About 2500 years passed without any advance in delivery system development, when the Arab physician Rhazes, 865-925 A.D., invented the coated pill. About a century later the Persian Avicenna, 980-1037 A.D., coated pills with gold or silver for increasing patient acceptability and for enhancing the effectiveness of the drug. Also around this time the first tablet was described in Arabian manuscripts written by al-Zahrawi, 936-1009 A.D. The manuscripts described a tablet formed from the follow impressions in two facing tablet molds. Pharmacy and medicine waited about 800 years for the next innovation in delivery systems, when in 1883 Mothes invented the capsule for administering drug. The next quantum leap in dosage forms came in 1972 with the invention of the osmotic delivery system by inventors Theeuwes and Higuchi as disclosed in U.S. Pat. Nos. 3,845,770 and 3,916,899. The osmotic system disclosed in those patents comprise a semipermeable wall that surrounds a compartment containing a useful agent. The wall is permeable to the passage of an external fluid, and it is substantially impermeable to the passage of useful agent. There is an osmotic passageway through the wall for delivering the useful agent from the osmotic system. These systems release a useful agent by fluid being imbibed through the semipermeable wall into the compartment at a rate determined by the permeability of the semipermeable wall and the osmotic pressure gradient across the semipermeable wall to produce an aqueous solution containing useful agent that is dispensed through the passageway from the system. These systems are extraordinarily effective for delivering a useful agent that is soluble in the fluid and exhibits an osmotic pressure gradient across the semipermeable wall against the external fluid.

A pioneer advancement in osmotic delivery systems, manufactured in the form of an osmotic device, was presented to the dispensing arts by inventor Felix Theeuwes in U.S. Pat. No. 4,111,202. In this patent, the delivery kinetics of the osmotic device are enhanced for delivering useful agents, including drugs that are insoluble to very soluble in the fluid, by manufacturing the osmotic device with a useful agent compartment and an osmagent compartment separated by an internal film. The internal film is movable from a rested to an expanded state. The osmotic device delivers agent by fluid being imbibed through the semipermeable wall into the osmagent compartment producing a solution that causes the compartment to increase in volume and act as a driving force that is applied against the film. This force urges the film to expand in the device against the useful agent compartment and, correspondingly, diminish the volume of the useful agent compartment whereby useful agent is dispensed through the passageway from the osmotic device. While this device operates successfully for its intended use, and while it can deliver numerous useful agents of varying solubilities, its use can be limited because of the manufacturing steps and costs needed for fabricating and placing the movable film in the compartment of the osmotic device.

In U.S. Pat. No. 4,327,725 patentees Richard Cortese and Felix Theeuwes provided an osmotic dispensing device for delivering beneficial agents that, because of its solubilities in aqueous and biological fluids, are difficult to deliver in meaningful amounts at controlled rates over time. The osmotic devices of this patent comprise a semipermeable wall surrounding a compartment containing a beneficial agent that is insoluble to very soluble in aqueous and biological fluids and an expendable hydrogel. In operation, the hydrogel expands in the presence of external fluid that is imbibed into the device and in some operations mixes with the beneficial agent, thereby forming a dispensable formulation that is dispensed through the passageway from the device. This device operates successfully for its intended use, and it delivers many difficult to deliver beneficial agents for their intended purpose. Now it has been observed, its use can be limited because the hydrogel can lack a present ability to imbibe sufficient fluid for the maximum self-expansion needed for urging all beneficial agent from the device.

It will be appreciated by those versed in the dispensing art, that if an osmotic device can be provided that exhibits a high level of osmotic activity for delivering a beneficial agent by generating in situ an expanding force sufficient for delivering the maximum amount of agent at a controlled rate such as osmotic device would have a positive value and represent an advancement in the dispensing art. Likewise, it will be immediately appreciated by those versed in the dispensing art that if an osmotic device is made available possessing dual thermodynamic osmotic activity for delivering increased amounts of a beneficial agent, said osmotic device would find practical application in the fields of pharmacy and medicine.

OBJECT OF THE INVENTION

Accordingly, in view of the above presentation, it is an immediate object of this invention to provide an osmotic system that can be manufactured by standard manufacturing techniques into osmotic devices of various sizes, shapes and forms that represent a further improvement and advancement in the dispensing art.

Another object of the invention is to provide an osmotic system manufactured in the form of an osmotic device for delivering in vivo a beneficial drug that is difficult to deliver and now can be delivered by the osmotic device in therapeutically effective amounts over time.

Another object of the invention is to provide an osmotic system possessing dual osmotic activity that operates as a unit, which system comprises a compartment containing a first osmotic composition comprising a drug, an osmagent and an osmopolymer, and a second osmotic composition comprising an osmagent and an osmopolymer, with the compositions acting in concert for delivering the drug through an osmotic passageway from the osmotic device.

Yet another object of the invention is to provide an osmotic device having means for high loading of a water insoluble or a slightly water soluble drug and means for delivering the drug in either instance at a controlled rate and continuously over time to a drug recipient.

Yet another object of the invention is to provide an osmotic device that can deliver a pH dependent beneficial agent by providing a neutral medium for delivering the beneficial agent in a finely dispersed form for increasing its surface area and for maximizing the dissolution rate of the beneficial agent.

Still yet another object of the invention is to provide an osmotic system for delivering a drug having a very low dissolution rate that is the rate limiting step for delivering the drug from the system, but now can be delivered by using an osmotic composition that functions in situ as a carrier, or a suspension agent, as a wetting agent and a solubilizing agent for increasing the dissolution rate and the solubility of the drug, thereby enhancing its delivery from the osmotic system.

Still yet another object of the invention is to provide an osmotic system comprising means for maintaining a high level of osmotic activity of a polymer used for delivering a beneficial agent from the osmotic system.

A further object of the invention is to provide an osmotic, therapeutic device that can administer a complete pharmaceutical dosage regimen comprising poorly soluble to very soluble agents, at a controlled rate and continuously for a particular time period, the use of which requires intervention only for the initiation and possibly for the termination of the regimen.

Still a further object of the invention is to provide an osmotic device that possesses the ability to deliver a broad range of drug delivery rates and simultaneously can deliver the drug according to a predetermined drug time release pattern to a biological recipient over time.

Other objects, features, aspects and advantages of the invention will be more apparent to those versed in the dispensing art from the following detailed specification taken in conjunction with the figures and the accompanying claims.

BRIEF DESCRIPTION OF THE DRAWINGS

In the drawings, which are not drawn to scale, but are set forth to illustrate various embodiments of the invention, the drawing figures are as follows.

In the drawings and the specification, like parts in related figures are identified by like parts. The terms appearing earlier in the specification and in the description of the drawings, as well as embodiments thereof, are further detailed elsewhere in the disclosure.

DETAILED DESCRIPTION OF THE DRAWINGS

Figure 1:
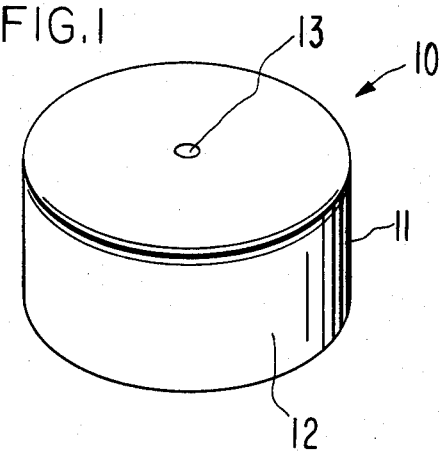
FIG. 1 is an isometric view of an osmotic device designed for orally administering a beneficial agent to the gastrointestinal tract.

Turning now to the drawings in detail, which are examples of various osmotic devices provided by the invention, and which examples are not to be construed as limiting, one example of an osmotic device is seen in FIG. 1. In FIG. 1, osmotic device 10 is seeen comprising a body member 11 having a wall 12 and a passageway 13 for releasing a beneficial agent from osmotic device 10.

Figure 2:
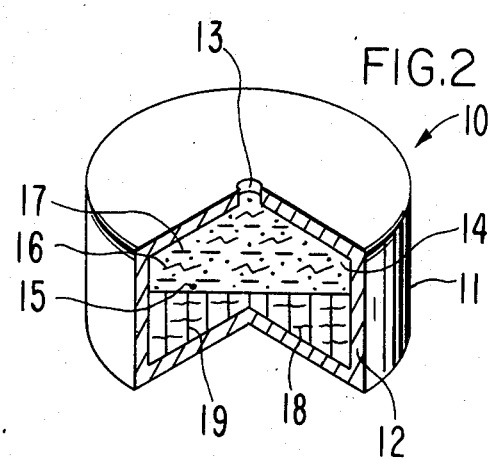
FIG. 2 is an opened view of the osmotic device of FIG. 1 illustrating the structure of the osmotic device of FIG. 1.

In FIG. 2, osmotic device 10 of FIG. 1 is seen in opened section. In FIG. 2, osmotic device 10 comprises a body 11, a semipermeable wall 12 that surrounds and forms internal compartment 14, that communicates through a passageway 13 with the exterior of osmotic device 10. Compartment 14 contains a first osmotic composition comprising a beneficial agent 15, represented by dots, which agent 15 can be from insoluble to very soluble in fluid imbibed into compartment 14, an osmagent 16, represented by wavy lines, that is soluble in fluid imbibed into compartment 14 and exhibits an osmotic pressure gradient across semipermeable wall 12 against an external fluid, and, an osmopolymer 17, represented by horizontal dashes, that imbibes fluid into compartment 14 and exhibits an osmotic pressure gradient across semipermeable wall 12 against an exterior fluid present in the environment of use. Wall 12 is formed of a semipermeable composition that is substantially permeable to the passage of the exterior fluid, and it is substantially impermeable to the passage of agent 15, osmagent 16 and osmopolymer 17. Semipermeable wall 12 is non-toxic and it maintains its physical and chemical integrity during the delivery life of device 10.

Compartment 14 also houses a second osmotic composition that is distant from passageway 13 and in contacting relation with the first composition. The second composition is an expandable driving force that acts in cooperation with the first expandable osmotic composition for delivering the maximum amount of beneficial agent 15 from osmotic device 10. The second osmotic composition comprises an osmagent 18, that is soluble in fluid imbibed into compartment 14 and exhibits an osmotic pressure gradient across semipermeable wall 12 against an external fluid, blended with an osmopolymer 19 that imbibes fluid into compartment 14 and exhibits an osmotic pressure gradient across semipermeable wall 12 against external fluid. Osmopolymer 17 and osmopolymer 19 are hydrophilic water soluble or lightly cross-linked water insoluble polymers, and they possess osmotic properties such as the ability to imbibe external fluid through the semipermeable wall, exhibit an osmotic pressure gradient across the semipermeable wall against the external fluid, and swell or expand in the presence of the fluid in the compartment. Osmopolymers 17 and 19 are mixed with osmagent 16 and 18, respectively, for imbibing the maximum volume of external fluid into compartment 14. This fluid is available to osmopolymers 17 and 19 to optimize the volumetric rate and for total expansion of osmopolymers 17 and 19. That is, osmopolymers 17 and 19 absorb fluid imbibed into compartment 14 by the osmotic imbibition action of osmopolymers 17 and 19 supplemented by the osmotic imbibition action of osmagents 16 and 18 for effecting the maximum expansion of osmopolymers 17 and 19 to an enlarged state.

In operation, the delivery of beneficial agent 15 from osmotic device 10 is carried out, in one presently preferred embodiment, by (1) imbibition of fluid by the first composition to form a fluid composition in situ and delivery of the fluidic composition through the passageway; and concurrently by (2) imbibition of fluid by the second composition causing the second composition to swell and cooperate with the first composition for driving the agent suspension through the passageway. According to the operation described, the osmotic device may be visualized as a cylinder, with the second composition expanding like the movement of a piston for aiding in delivering the agent composition from the osmotic device. For the purpose of the present analysis, the volume rate delivered by the osmotic device $F_t$ is composed of two sources; the water imbibition rate by the first composition F, and the water imbibition rate by the second composition Q wherein:

$$F_t = F + Q \quad (1)$$

Since the boundary between the first composition and the second composition hydrates very little during the functioning of the osmotic device, there is insignificant water migration between the compositions. Thus, the water imbibition rate of the second composition, Q, equals the expansion of its volume:

$$\frac{dv_p}{dt} = Q \quad (2)$$

The total delivery rate from the osmotic device is then, $$\frac{dm}{dt} = F_t \cdot C = (F + Q)C \quad (3)$$

wherein C is the concentration of beneficial agent in the delivered slurry. Conservation of the osmotic device volume, V, and the surface area, A, gives equations (4) and (5):

$$V = V_d + V_p \quad (4)$$

$$A = A_d + A_p \quad (5)$$

wherein $V_d$ and $V_p$ equal the volumes of the first composition and the second composition, respectively; and wherein $A_d$ and $A_p$ equal the surface area contact with the wall by the first composition and the second composition, respectively. In operation, both $V_p$ and $A_p$ increase with time, while $V_d$ and $A_d$ decrease with time as the device delivers beneficial agent.

The volume of the second composition that expands with time when fluid is imbibed into the compartment is given by equation (6):

$$V_p = f\left(\frac{W_H}{W_p}\right) \quad (6)$$

wherein $W_H$ is the weight of fluid imbibed by the second composition, $W_p$ is the weight of the second composition initially present in the device, $W_H/W_p$ is the ratio of fluid to initial solid of the second composition, and $$V_p = \left(1 + \frac{W_H}{W_p}\right)\frac{W_p}{\rho} \quad (7)$$

wherein $\rho$ is the density of the second composition corresponding to $W_H/W_p$. Thus, based on the geometry of a cylinder, where r is the radius of the cylinder, the area of imbibition is related to the volume of the swollen second composition as follows:

$$A_p = \pi r^2 + \frac{2}{r} \frac{W_p}{\rho}(1 + W_H/W_p) \quad (8)$$

$$A_d = A - A_p \quad (9)$$

The fluid imbibition rates into each composition are:

$$F = \left(\frac{k}{h}\right)(A_d \cdot \Delta \pi_d) \quad (10)$$

$$Q = \left(\frac{k}{h}\right)(A_p \cdot \Delta\pi_p) \tag{11}$$

wherein k equals the osmotic permeability of the wall, h equals the wall thickness, $\Delta\pi_d$ and $\Delta\pi_p$ are the osmotic gradients for the first composition and the second composition, respectively. The total delivery rate, therefore, is:

$$\frac{dm}{dt} = \frac{k}{h} C \left\{ \left[ A - \pi r^2 - \frac{2}{r} \frac{W_p}{\rho}(1 + W_H/W_p) \right] \Delta\pi_d + \left[ \pi r^2 + \frac{2}{r} \frac{W_p}{\rho}(1 + W_H/W_p) \right] \Delta\pi_p \right\} \tag{12}$$

Figure 3:
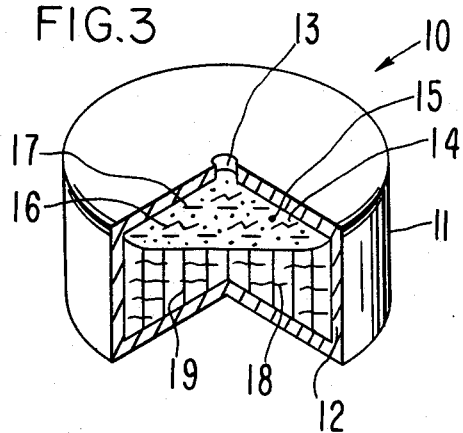
FIG. 3 is an opened view of the osmotic device of FIG. 1 illustrating the osmotic device in operation and delivering a beneficial agent from the osmotic device.
Figure 4:
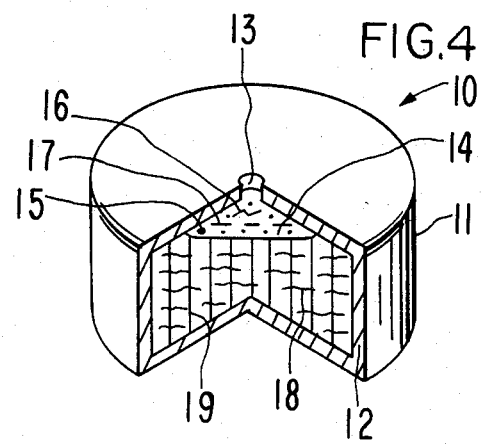
FIG. 4 is an opened view of the osmotic device of FIG. 1 considered with FIG. 3 illustrating the osmotic device in operation and delivering a major amount of a beneficial agent from the osmotic device.

FIGS. 3 and 4 illustrate the osmotic device in operation as described for FIGS. 1 and 2. In FIGS. 3 and 4, for osmotic device 10, fluid is imbibed by the first composition at a rate determined by the permeability of the wall and the osmotic pressure gradient across the wall. The imbibed fluid continuously forms a solution containing beneficial agent, or a solution of a gel of osmagent and osmopolymer containing beneficial agent in suspension, which solution or suspension in either operation is released by the combined operations of device 10. These operations include the solution, or the suspension being osmotically delivered through the passageway due to the continuous formation of solution or suspension, and by the swelling and increasing volume of the second composition, represented by the increase in height of the vertical lines in FIGS. 3 and 4. This latter swelling and increase in volume applies pressure against the solution or suspension thereby aiding the first composition and simultaneously causing delivery of beneficial agent to the exterior of the device. Thus, the osmotic device provided by this invention can be viewed as a single unit construction device comprising two compositions containing two polymeric structures acting in concert for effective drug administration to a patient.

The first composition and the second composition act together to substantially insure that delivery of beneficial agent from the compartment is constant over a prolonged period of time by two methods. First, the first composition imbibes external fluid across the wall, thereby forming either a solution or a suspension the latter which would be substantially delivered at nonzero order (without the second composition present), since the driving force decays with time. Second, the second composition operates by two simultaneous operations: (1) the second composition operates to continuously concentrate beneficial agent by imbibing some fluid from the first composition to help keep the concentration of beneficial agent from falling below saturation and, (2), the second composition by imbibing external fluid across the wall and creating continuous increases in volume, thereby exerting a force against the first composition and diminishing the volume of beneficial agent, thusly directing beneficial agent to the passageway in the compartment. Additionally, as the extra solution or suspension formed in the first composition is squeezed out, the osmotic composition closely contacts the internal wall and generates a constant osmotic pressure and, therefore, a constant delivery rate in conjunction with the second composition. The swelling and expansion of the second composition, with its accompanying increase in volume, along with the simultaneous corresponding reduction in volume of the first composition assures the delivery of beneficial agent at a controlled rate over time.

Device 10 of FIGS. 1 through 4 can be made into many embodiments including the presently preferred embodiments for oral use; for releasing either a locally or systemically acting therapeutic agent in a gastrointestinal tract. Oral system 10 can have various conventional shapes and sizes such as round with a diameter of 3/16 inches to ⅝ inches. In these forms system 10 can be adapted for administering beneficial agent to numerous animals, including warm blooded animals, humans, avians, reptiles and pisces.

Figure 5:
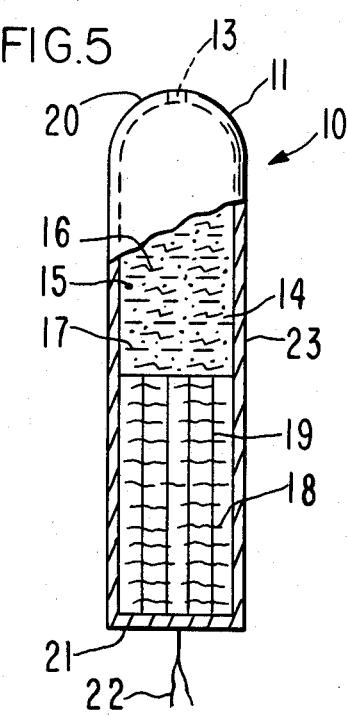
FIG. 5 shows an osmotic therapeutic device with its wall partially broken away, designed for delivering a beneficial agent into a body passageway, such as the ano-rectal and vaginal passageways.
Figure 6:
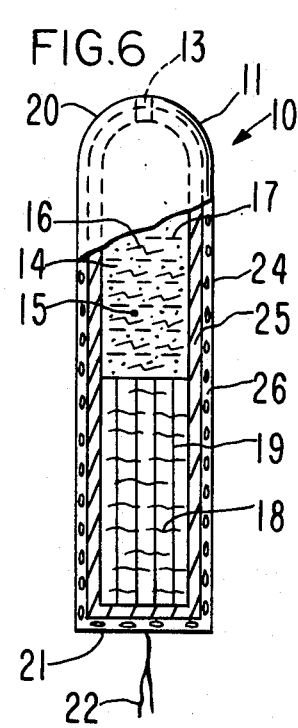
FIG. 6 shows the osmotic device of FIG. 5 with a different wall structure.
Figure 7:
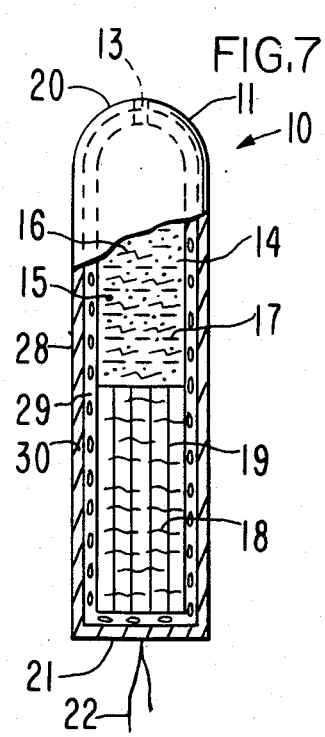
FIG. 7 shows the osmotic device of FIG. 5 depicting a different wall structure than the wall structure depicted in FIG. 6.

FIGS. 5, 6 and 7 show another embodiment provided by this invention. FIGS. 5, 6 and 7 show an osmotic device 10 designed for placement in a body passageway, such as a vagina, or the ano-rectal canal. Device 10 has an elongated, cylindrical, self-sustaining shape with a rounded lead end 20, a trailing end 21, and it is equipped with manually controlled strings 22 for easily removing device 10 from the biological passageway. Device 10 is structurally identical with the device described above in FIGS. 1 through 4, and it operates in a like manner. In FIG. 5, device 10 is depicted with a semipermeable wall 23, in FIG. 6 with a laminated wall 24 comprising an inner semipermeable lamina 25 adjacent to compartment 14 and an external microporous lamina 26 distant from compartment 14. In FIG. 7, device 10 comprises a laminated wall 28 formed of a microporous lamina 29 next to compartment 14, and a semipermeable lamina 30 facing the environment of use and in laminar arrangement with microporous lamina 29. The semipermeable lamina used for manufacturing these osmotic devices is permselective since it is permeable to the passage of fluid and substantially impermeable to the passage of agent, osmagent and osmopolymer. Device 10 delivers a beneficial agent for absorption by the vaginal mucosa, or the ano-rectal mucosa, to produce an in vivo local or systemic effect over a prolonged period of time.

The osmotic devices of FIGS. 1 through 7 can be used for delivering numerous agents including drugs at a controlled rate independent of the drug pH dependency, or where the dissolution rate of the agent can vary between low and high in fluid environments, such as gastric fluid and intestinal fluid. The osmotic devices also provide for the high loading of agents of low solubility and their delivery at meaningful, therapeutic amounts. While FIGS. 1 through 7 are illustrative of various osmotic devices that can be made according to the invention, it is to be understood these devices are not to be construed as limiting, as the devices can take a wide variety of shapes, sizes and forms adapted for delivering beneficial agents to the environment of use. For example, the devices include buccal, implant, artificial gland, cervical, intrauterine, ear, nose, dermal, subcutaneous, and like delivery devices. The devices also can be sized, shaped, structured and adapted for delivering an active agent in streams, aquariums, fields, factories, reservoirs, laboratory facilities, hot houses, transportation means, naval means, military means, hospitals, veterinary clinics, nursing homes, farms, zoos, sickrooms, chemical reactions, and other environments of use.

DETAILED DESCRIPTION OF THE INVENTION

In accordance with the practice of this invention it has now been found that osmotic delivery device 10 can be manufactured with a first osmotic composition and a second osmotic composition mutually housed in cooperative relationship in the compartment of the device. The compartment is formed by a wall semipermeable comprising a material that does not adversely affect the beneficial agent, osmagent, osmopolymer, and the like. The semipermeable wall is permeable to the passage of an external fluid such as water and biological fluids, and it is substantially impermeable to the passage of agents, osmagents, osmopolymers, and the like. The wall is formed of a material that does not adversely affect an animal, or host, or the components comprising the device, and the selectively semipermeable materials used for forming the wall are non-erodible and they are insoluble in fluids. Typical materials for forming the wall are in one embodiment cellulose esters, cellulose ethers and cellulose ester-ethers. These cellulosic polymers have a degree of substitution, D.S., on the anhydroglucose unit, from greater than 0 up to 3 inclusive. By degree of substitution is meant the average number of hydroxyl groups originally present on the anhydroglucose unit comprising the cellulose polymer that are replaced by a substituting group. Representative materials include a member selected from the group consisting of cellulose acylate, cellulose diacylate, cellulose triacylate, cellulose acetate, cellulose diacetate, cellulose triacetate, moni, di and tricellulose alkanylates, mono, di and tricellulose aroylates, and the like. Exemplary polymers include cellulose acetate having a D.S. up to 1 and an acetyl content up to 21%; cellulose acetate having an acetyl content of 32 to 39.8%; cellulose acetate having a D.S. of 1 to 2 and an acetyl content of 21 to 35%; cellulose acetate having a D.S. of 2 to 3 and an acetyl content of 35 to 44.8%, and the like. More specific cellulosic polymers include cellulose propionate having a D.S. of 1.8 and a propionyl content of 39.2 to 45% and a hydroxyl content of 2.8 to 5.4%; cellulose acetate butyrate having a D.S. of 1.8, an acetyl content of 13 to 15% and a butyryl content of 34 to 39%; cellulose acetate butyrate having an acetyl content of 2 to 29%, a butyryl content of 17 to 53% and a hydroxyl content of 0.5 to 4.7%; cellulose triacylates having a D.S. of 2.9 to 3 such as cellulose trivalerate, cellulose trilaurate, cellulose tripalmitate, cellulose trisuccinate, and cellulose trioctanoate; cellulose diacylates having a D.S. of 2.2 to 2.6 such as cellulose disuccinate, cellulose dipalmitate, cellulose dioclanoate, cellulose dipentale, co-esters of cellulose such as cellulose acetate butyrate and cellulose acetate propionate, and the like.

Additional semipermeable polymers include cellulose acetaldehyde dimethyl acetate, cellulose acetate ethyl carbamate, cellulose acetate methyl carbamate, cellulose acetate dimethyl aminoacetate, semipermeable polyamides, semipermeable polyurethanes, semipermeable sulfonated polystyrenes, semipermeable cross-linked selectively polymers formed by the coprecipitation of a polyanion and a polycation as disclosed in U.S. Pat. Nos. 3,173,876; 3,276,586; 3,541,005; 3,541,006; and 3,546,142; semipermeable polymers as disclosed by Loeb and Sourirajan in U.S. Pat. No. 3,133,132; semipermeable lightly cross-linked polystyrene derivatives; semipermeable crosslinked poly(sodium styrene sulfonate); semipermeable cross-linked poly(vinylbenzyl trimethyl amonium chloride); semipermeable polymers exhibiting a fluid permeability of $10^{-5}$ to $10^{-1}$ (cc.mil/cm$^2$.hr.atm) expressed per atmosphere $10^{-8}$ of hydrostatic or osmotic pressure difference across the semipermeable wall. The polymers are known to the art in U.S. Pat. Nos. 3,845,770; 3,916,899; and 4,160,020; and in *Handbook of Common Polymers* by Scott, J. R. and Roff, W. J., 1971, published by CRC Press, Cleveland, OH.

The laminated wall comprising a semipermeable lamina and a microporous lamina are in laminar arrangement and they act in concert to form an integral laminated wall that maintains its physical and chemical integrity and does not separate into the original lamina throughout the operative agent release history of the osmotic device. The semipermeable lamina is made from the semipermeable polymeric materials presented above, the semipermeable homopolymers, the semipermeable copolymers, and the like.

Microporous lamina suitable for manufacturing the laminated osmotic device generally comprises preformed microporous polymeric materials, and polymeric materials that can form a microporous lamina in the environment of use. The microporous materials in both embodiments are laminated to a semipermeable lamina to form the laminated wall. The preformed materials suitable for forming the microporous lamina area essentially inert, they maintain their physical and chemical integrity during the period of agent release and they can be described generically as having a sponge like appearance that provides a supporting structure for a semipermeable lamina and also provides a supporting structure for microscopic sized interconnected pores or voids. The materials can be isotropic wherein the structure is homogeneous throughout a cross sectional area, or they can be anisotropic wherein the structure is non-homogeneous throughout a cross sectional area. The pores can be continuous pores that have an opening on both faces of microporous lamina, pores interconnected through totuous paths of regular and irregular shapes, including curved, curved-linear, randomly oriented continuous pores, hindered connected pores and other porous paths discernible by microscopic examination. Generally, microporous lamina are defined by the pore size, the number of pores, the tortuosity of the microporous path and the porosity which relates to the size and the number of pores. The pore size of a microporous lamina is easily ascertained by measuring the observed pore diameter at the surface of the material under the electron microscope. Generally, materials possessing from 5% to 95% pores and having a pore size of from 10 angstroms to 100 microns can be used for making a microporous lamina. The pore size and other parameters characterizing the microporous structure also can be obtained from flow measurements, where a liquid flux, J, is produced by a pressure difference $\Delta P$, across the lamina. The liquid flux through a lamina with pores of uniform radius extended through the lamina and perpendicular to its surface with area A given by relation (13):

$$J = \frac{N\pi r^4 \Delta P}{8\eta \Delta x} \quad (13)$$

wherein J is the volume transported per unit time and lamina area containing N number of pores of radius r, $\rho$ is the viscosity of the liquid and $\Delta P$ is the pressure difference across the lamina with thickness $\Delta x$. For this type of lamina, the number of pores N can be calculated from relation (14), wherein $\epsilon$ is the porosity defined as the ratio of void volume to total volume of the lamina; and A is the cross sectional area of the lamina containing N pores.

$$N = \frac{\epsilon A}{\pi r^2} \quad (14)$$

The pore radius then is calculated from relation (15):

$$r = \left[ 8 \eta \frac{\Delta x \tau}{\Delta P \epsilon} J' \right]^{\frac{1}{2}} \quad (15)$$

wherein J' is the volume flux through the lamina per unit area produced by the pressure difference $\Delta P$ across the lamina, $\rho$, $\epsilon$ and $\Delta x$ have the meaning defined above and $\tau$ is the tortuosity defined as the ratio of the diffusional path length in the lamina to the lamina thickness. Relations of the above type are discussed in *Transport Phenomena In Membranes,* by Lakshminatayanaiah, N. Chapter 6, 1969, published by Academic Press, Inc., New York.

As discussed in this reference, supra, on page 336, in Table 6.13, the porosity of the lamina having pores with radius r can be expressed relative to the size of the transported molecule having a radius a, and as the ratio of molecular radius to pore radius a/r decreases, the lamina becomes porous with respect to this molecule. That is, when the ratio a/r is less than 0.3, the lamina becomes substantially microporous as expressed by the osmotic reflection coefficient $\sigma$ which decreases below 0.5. Microporous lamina with a reflection coefficient $\sigma$ in the range of less than 1, usually from 0 to 0.5, and preferably less than 0.1 with respect to the active agent are suitable for fabricating the system. The reflection coefficient is determined by shaping the material in the form of a lamina and carrying out water flux measurements as a function of hydrostatic pressure difference and as a function of the osmotic pressure difference caused by the active agent. The osmotic pressure difference creates a hydrostatic volume flux, and the reflection coefficient is expressed by relation (16):

$$\sigma = \frac{\text{osmotic volume flux}}{\text{hydrostatic volume flux}} \quad (16)$$

Properties of microporous materials are described in *Science,* Vol. 170, 1970, pp 1302–1305; *Nature,* Vol. 214, 1967, page 285; *Polymer Engineering and Science,* Vol. 11, 1971, pp 284–288; U.S. Pat. Nos. 3,567,809 and 3,751,536; and in *Industrial Processing With Membranes,* by Lacey, R. E., and Loeb, Sidney, 1972, pp 131–134.

Microporous materials having a preformed structure are commercially available and they can be made by art known methods. The microporous materials can be made by etching, nuclear tracking, by cooling a solution of flowable polymer below the freezing point whereby solvent evaporates from the solution in the form of crystals dispersed in the polymer and then curing the polymer followed by removing the solvent crystals, by cold or hot stretching at low or high temperatures until pores are formed, by leaching from a polymer a soluble component by an appropriate solvent, by ion exchange reaction, and by polyelectrolyte process. Process for repairing microporous materials are described in *Synthetic Polymer Membranes,* by R. E. Kesting, Chapters 4 and 5, 1971, published by McGraw Hill, Inc.; *chemical Reviews,* Ultrafiltration, Vol. 18., pp 373 to 455, 1934; *Polymer Eng. and Sci.,* Vol. 11. No. 4, pp 284–288, 1971; *J. Appl. Poly. Sci.,* Vol. 15, pp 811–829, 1971; and in U.S. Pat. Nos. 3,565,259; 3,615,024; 3,751,536; 3,801,692; 3,852,224, and 3,849,528.

Microporous materials useful for making the lamina include microporous polycarbonates comprised of linear polyesters of carbonic acid in which carbonate groups recur in the polymer chain; microporous materials prepared by the phosgenation of a dihydroxyl aromatic, such as bisphenol A; microporous poly(vinyl chloride); microporous polyamides such as polyhexamethylene adipamide; microporous modacrylic copolymers including those formed from poly(vinylchloride) 60% and acrylonitrile; styrene acrylic and its copolymers; porous polysulfones characterized by diphenylene sulfone groups in a linear chain thereof; halogenated poly(vinylidene); polychloroethers; acetal polymers; polyesters prepared by esterification of a dicarboxylic acid or anhydride with an alkylene polyol; poly(alkylenesulfides); phenolic polyesters; microporous poly(saccharides); microporous poly(saccharides) having substituted and unsubstituted anhydroglucose units exhibiting an increased permeability to the passage of water and biological fluids than a nonporous semipermeable lamina; asymmetric porous polymers; cross-linked olefin polymers; hydrophobic or hydrophilic microporous homopolymers, copolymers or interpolymers having a reduced bulk density; and materials described in U.S. Pat. Nos. 3,597,752; 3,643,178; 3,654,066; 3,709,774; 3,718,532; 3,803,061; 3,852,224; 3,853,601; and 3,852,388; in British Patent No. 1,126,849, and in *Chem. Abst.,* 1969, Vol. 71 4274F, 22572F, 22573F.

Additional microporous materials include microporous poly(urethanes); microporous cross-linked, chain extended poly(urethanes); microporous poly(urethanes) in U.S. Pat. No. 3,524,753; microporous poly(imides); microporous poly(benzimidazoles); regenerated microporous proteins; semi-solid cross-linked microporous poly(vinylpyrrolidone); microporous materials prepared by diffusion of multivalent cations into polyelectrolyte sols as in U.S. Pat. No. 3,565,259; anisotropic microporous materials of ionically associated polyelectrolytes; porous polymers formed by the coprecipitation of a polycation and a polyanion as described in U.S. Pat. Nos. 3,276,589; 3,541,055; 3,541,066 and 3,546,142; derivatives of poly(styrene), such as microporous poly(sodium styrenesulfonate) and microporous poly(vinyl benzyltrimethyl-ammonium chloride); the microporous materials disclosed in U.S. Pat. No. 3,615,024; and U.S. Pat. Nos. 3,646,178 and 3,852,224.

Further, the micropore forming material used for the purpose of the invention includes the embodiment wherein the microporous lamina is formed in situ by a pore former being removed by dissolving or leaching it to form the microporous lamina during the operation of the system. The pore former can be a solid or a liquid. The term liquid, for this invention, embraces semi-solids and viscous fluids. The pore formers can be inorganic or organic. The pore formers suitable for the invention include pore formers that can be extracted without any chemical change in the polymer. The pore forming solids have a size of about 0.1 to 200 micrometers and they include alkali metal salts such as sodium chloride, sodium bromide, potassium chloride, potassium sulfate, potassium phosphate, sodium benzoate, sodium acetate, sodium citrate, potassium nitrate, and the like. The alkali earth metal salts include calcium phosphate, calcium nitrate, and the like. The transition metal salts include ferric chloride, ferrous sulfate, zinc sulfate, cupric chloride, manganese, fluoride, manganese fluorosilicate, and the like. The pore formers include organic compounds such as polysaccharides. The polysaccharides include the sugars: succrose, glucose, fructose, mannitol, mannose, galactose, aldohexose, altrose, talose, sorbitol, lactose, monosaccharides and disaccharides. Also, organic aliphatic and aromatic oils and solids, including diols and polyols, as exemplified by polyhydric alcohols, poly(alkylene glycols), polyglycols, alkylene glycols, poly($\alpha$-$\omega$)-alkylenediols esters or alkylene glycols and the like; water soluble cellulosic polymers such as hydroxyloweralkyl cellulose, hydroxypropyl methylcellulose, methyl cellulose, methylethyl cellulose, hydroxyethyl cellulose and the like; water soluble polymers such as polyvinylpyrrolidone, sodium carboxymethylcellulose and the like. The pore-formers are nontoxic and on their removal from the lamina channels are formed through the lamina. In a preferred embodiment the non-toxic, poreforming agents are selected from the group consisting of inorganic and organic salts, carbohydrates, polyalkylene glycols, poly-($\alpha$-$\omega$)-alkylene-diols, esters of alkylene glycols, glycols and water soluble polymers used for for forming a microporous lamina in a biological environment. Generally, for the purpose of this invention, when the polymer forming the lamina contains more than 15% by weight of a poreformer, the polymer is a precursor microporous lamina that on removing the poreformer yields a lamina which is substantially microporous.

The expression passageway as used herein comprises means and methods suitable for releasing the agent or drug from the osmotic system. The expression includes osmotic aperture, osmotic orifice, osmotic hole or osmotic bore through the semipermeable wall or the laminated wall. The osmotic passageway can be formed by mechanical drilling, laser drilling or by eroding an erodible element such as a gelatin plug in the environment of use. A detailed description of osmotic passageways, and the maximum and minimum dimensions for a passageway, are disclosed in U.S. Pat. Nos. 3,845,770 and 3,916,899. The osmotic passageway has a maximum cross-sectional area, $A_s$, defined by the relation (17) as follows:

$$A_{s(max)} = \frac{L}{F} \times \frac{Q_p}{t} \times \frac{1}{DS} \qquad (17)$$

wherein L is the length of the passageway $Q_p/t$ is the mass delivery rate of the agent, D is the diffusion coefficient of the agent, S is the solubility of the agent in the fluid, and F is from 2 to 1000, said passageway having a minimum area $A_s$ defined by relation (18) as follows:

$$A_{s(min)} = \left[\frac{Lv}{t} \times 8 \times \frac{\pi\eta}{\Delta P}\right]^{\frac{1}{2}} \qquad (18)$$

wherein L is the length of the passageway, v/t is the agent solution volume delivery rate, $\pi$ is 3.14; $\rho$ is the viscosity of agent solution dispensed from the device and $\Delta P$ is the hydrostatic pressure difference between the inside and the outside of the compartment having a value up to 20 atmospheres.

The osmotically effective compounds that can be used for the purpose of this invention include inorganic and organic compounds that exhibit an osmotic pressure gradient across the semipermeable wall, or across a semipermeable microporous laminated wall, against an external fluid. The osmotically effective compounds, along with the osmopolymers, imbibe fluid into the osmotic device thereby making available in situ fluid for imbibition by an osmopolymer to enhance its expansion, and/or for forming a solution or suspension containing a beneficial agent for its delivery through the passageway from the osmotic device. The osmotically effective compounds are known also as osmotically effective solutes, or osmagents. The osmotically effective compounds are used by mixing them with a beneficial agent and osmopolymer for forming a solution, or suspension containing the beneficial agent that is osmotically delivered from the device. The expression limited solubility as used herein means the agent has a solubility of about less then 5% by weight in the aqueous fluid present in the environment. The osmotic solutes are used by homogeneously or heterogeneously mixing the solute with the agent or osmopolymer and then charging them into the reservoir. The solutes and osmopolymers attract fluid into the reservoir producing a solution of solute in a gel which is delivered from the system concomitantly transporting undissolved and dissolved beneficial agent to the exterior of the system. Osmotically effective solutes used for the former purpose include magnesium sulfate, magnesium chloride, potassium sulfate, sodium sulfate, lithium sulfate, potassium acid phosphate, d-mannitol, urea, inositol, magnesium succinate, tartaric acid, carbohydrates such as raffinose, sucrose, glucose, $\alpha$-d-lactose monohydrate, and mixtures thereof. The amount of osmagent in the compartment will generally be from 0.01% to 30% or higher in the first composition, and usually from 0.01% to 40% or higher in the second composition.

The osmotic solute is initially present in excess and it can be in any physical form that is compatible with the beneficial agent, the osmagent, and osmopolymer. The osmotic pressure of saturated solutions of various osmotically effective compounds and for mixtures of compounds at 37° C., in water, is listed in Table 1. In the table, the osmotic pressure $\pi$, is in atmospheres, atm. The osmotic pressure is measured in a commercially available osmometer that measures the vapor pressure difference between pure water and the solution to be analyzed and, according to standard thermodynamic principles, the vapor pressure ratio is converted into osmotic pressure difference. In Table 1, osmotic pressures of from 20 atm to 500 atm are set forth. Of course, the invention includes the use of lower osmotic pressures from zero, and higher osmotic pressures than those set forth by way of example in Table 1. The osmometer used for the present measurements is identified as Model 320B, Vapor Pressure Osmometer, manufactured by the Hewlett Packard Co., Avondale, PA.

TABLE 1

| COMPOUND OR MIXTURE | OSMOTIC PRESSURE ATM |
| --- | --- |
| Lactose-Fructose | 500 |
| Dextrose-Fructose | 450 |
| Sucrose-Fructose | 430 |
| Mannitol-Fructose | 415 |
| Sodium Chloride | 356 |

TABLE 1-continued

| COMPOUND OR MIXTURE | OSMOTIC PRESSURE ATM |
| --- | --- |
| Fructose | 355 |
| Lactose-Sucrose | 250 |
| Potassium Chloride | 245 |
| Lactose-Dextrose | 225 |
| Mannitol-Dextrose | 225 |
| Dextrose-Sucrose | 190 |
| Manitol-Sucrose | 170 |
| Dextrose | 82 |
| Potassium Sulfate | 39 |
| Mannitol | 38 |
| Sodium Phosphate Tribasic 12H$_2$O | 36 |
| Sodium Phosphate Dibasic 7H$_2$O | 31 |
| Sodium Phosphate Dibasic 12H$_2$O | 31 |
| Sodium Phosphate Dibasic Anhydrous | 29 |
| Sodium Phosphate Monobasic H$_2$O | 28 |

The osmopolymers suitable for forming the first osmotic composition, and also suitable for forming the second osmotic composition, are osmopolymers that exhibit fluid imbibition properties. The osmopolymers are swellable, hydrophilic polymers which osmopolymers interact with water and aqueous biological fluids and swell or expand to an equilibrium state. The osmopolymers exhibit the ability to swell in water and retain a significant portion of the imbibed water within the polymer structure. The osmopolymers swell or expand to a very high degree, usually exhibiting a 2 to 50 fold volume increase. The osmopolymers can be noncross-linked or cross-linked. The swellable, hydrophilic polymers are in one presently preferred embodiment lightly cross-linked, such cross-links being formed by covalent or ionic bonds. The osmopolymers can be of plant, animal or synthetic origin. The osmopolymers are hydrophilic polymers. Hydrophilic polymers suitable for the present purpose include poly(hydroxyalkyl methacrylate) having a molecular weight of from 30,000 to 5,000,000; poly(vinylpyrrolidone) having molecular weight of from 10,000 to 360,000; anionic and cationic hydrogels; polyelectrolyte complexes; poly(vinyl alcohol) having a low acetate residual, cross-linked with glyoxal, formaldehyde, or glutaraldehyde and having a degree of polymerization from 200 to 30,000; a mixture of methyl cellulose, cross-linked agar and carboxymethyl cellulose; a water insoluble, water swellable copolymer reduced by forming a dispersion of finely divided copolymer of maleic anhydride with styrene, ethylene, propylene, butylene or isobutylene cross-linked with from 0.001 to about 0.5 moles of polyunsaturated cross-linking agent per mole of maleic anhydride in the copolymer; water swellable polymers of N-vinyl lactams, and the like.

Other osmopolymers include polymers that form hydrogels such as Carbopol ® acidic carboxy polymers having a molecular weight of 450,000 to 4,000,000; Cyanamer ® polyacrylamides; cross-linked water swellable indene-maleic anhydride polymers; Goodrite ® polyacrylic acid having a molecular weight of 80,000 to 200,000; Polyox ® polyethylene oxide polymers having a molecular weight of 100,000 to 5,000,000; starch graft copolymers; Aqua-Keeps ® acrylate polymer; diester cross-linked polyglucan, and the like. Representative polymers that form hydrogels are known to the prior art in U.S. Pat. No. 3,865,108 issued to Hartop; U.S. Pat. No. 4,002,173 issued to Manning; U.S. Pat. No. 4,207,893 issued to Michaels; and in *Handbook of Common Polymers*, by Scott and Roff, published by the Chemical Rubber Company, Cleveland, OH. The amount of osmopolymer in the first osmotic composition is about 0.01 to 90%, and the amount of osmopolymer in the second osmotic composition is 15 to 95%. In a presently preferred embodiment, the osmopolymer identified as $P_1$ comprising the first composition can be different than the osmopolymer identified as $P_2$ comprising the second composition. The osmopolymer in the first composition can be structurally different than the osmopolymer in the second composition, or the osmopolymers can be substantially structurally identical with the molecular weight of the osmopolymer in the second osmotic composition larger than the molecular weight of the osmopolymer in the first osmotic composition. The osmopolymer $P_1$ comprising the first composition serves as a pharmaceutically acceptable carrier for the active agent and it contributes to the driving force that cooperates with osmopolymer $P_2$ comprising the second composition that delivers the agent through the passageway from the device. During operation of the device fluid is imbibed into the device resulting in the viscosity of $P_2$ being greater than the viscosity of $P_1$. In this operation $P_1$ and $P_2$ operate as a single unit substantially free of a void between the interfaced contacting surfaces of osmopolymer $P_1$ and $P_2$ for successful delivery of the beneficial agent from the osmotic device.

Osmopolymer fluid imbibition determination for a chosen polymer can be made by following the procedure described below. A $\frac{1}{2}$ inch round disk, fitted with a $\frac{1}{8}$ inch diameter stainless steel plug, is charged with a known quantity of polymer with the plugs extending out either end. The plugs and the die were placed in a Carver press with plates between 200° F. and 300° F. A pressure of 10,000 to 15,000 psi was applied to the plugs. After 10 to 20 minutes of heat and pressure the electrical heating to the plates was turned off, and tap water circulated through the plates. The resulting $\frac{1}{2}$ inch disks were placed in an air suspension coater charged with 1.8 kg saccharide cores and coated with cellulose acetate having an acetyl content of 39.8% dissolved in 94:6 w/w, $CH_2Cl_2/CH_3OH$, to yield a 3% w/w solution. The coated systems were dried overnight at 50° C. The coated disks were immersed in water at 37° C. and periodically removed for a gravimetric determination of water imbibed. The initial imbibition pressure was calculated by using the water transmission constant for the cellulose acetate, after normalizing imbibition values for membrane surface area and thickness. The polymer used in this determination was the sodium derivative of Carbopol-934 ® polymer, prepared according to the procedure of B. F. Goodrich Service Bulletin GC-36, "Carbopol ® Water-Soluble Resins", page 5, published by B. F. Goodrich, Akron, OH.

The cumulative weight gain values, y, as a function of time, t, for the water soluble polymer disk coated with the cellulose acetate were used to determine the equation of the line $y = c + bt + at^2$ passing through those points by at least square fitting technique.

The weight gain for the Na Carbopol-934 ® is given by the equation (19) that follows: Weight gain equals $0.359 + 0.665t - 0.00106t^2$ wherein t is elapsed time in minutes. The rate of water flux at any time will be equal to the slope of the line that is given by the following equations (19) and (20):

$$\frac{dy}{dt} = \frac{d(0.359 + 0.665t - 0.00106t^2)}{dt} \tag{19}$$

-continued $$\frac{dy}{dt} = 0.665 - 0.00212t \qquad (20)$$

To determine the initial rate of water flux the derivative is evaluated at t=0, and dy/dt=0.665 μl/min., which is equal to the coefficient b. Then, normalizing the imbibition rate for time, membrane surface area and thickness, and the membrane permeability constant to water, Kπ may be determined according to the following equation (21):

$$K\pi = 0.665 \ \mu l/min. \times \left(\frac{60 \ min.}{hr}\right) \times \left(\frac{1 \ ml}{1000 \ l}\right) \left(\frac{0.008 \ cm}{2.86 \ cm}\right) \qquad (21)$$

with $K = 1.13 \times 10^{-4}$ cm$^2$/hr. The π value for NaCl was determined with a Hewlett Packard vapor pressure osmometer to be 345 atm±10%, and the K value for cellulose acetate used in this experiment calculated from NaCl imbibition values was determined to be $1.9 \times 10^{-7}$ cm$^2$/hr atm.

Figure 8:
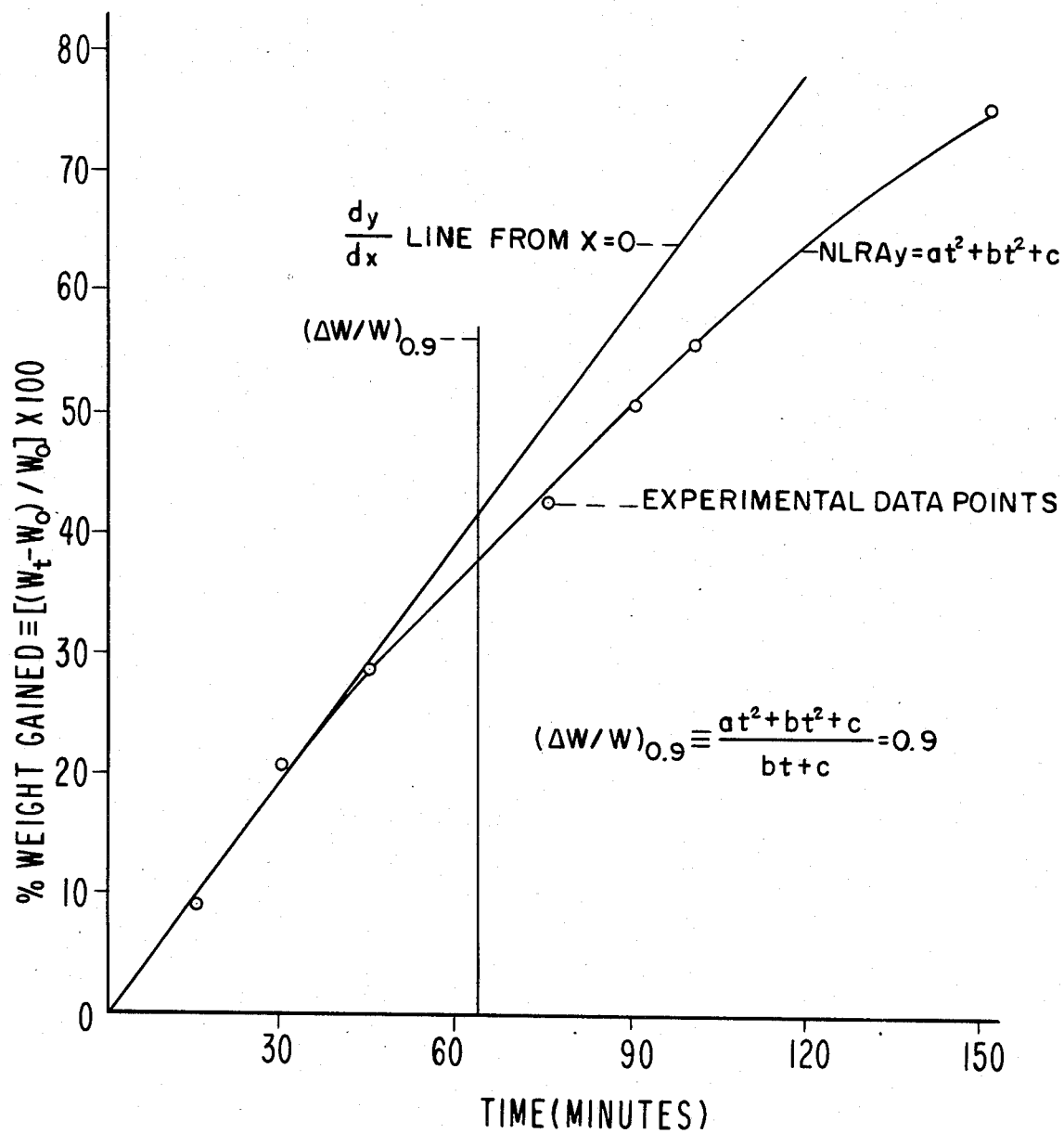
FIG. 8 represents the weight gain as a function of time for a polymer encapsulated in a semipermeable membrane when the encapsulated polymer is placed in water.

Substituting these values into the calculated Kπ expression, $(1.9 \times 10^{-7}/cm^2/hr.atm)(\pi) = 1.13 \times 10^{-4}$ cm$^2$hr gives π=600 atm at t=0. As a method for evaluating the efficiency of a polymer with respect to duration of zero order driving force, the percent of water uptake was selected before the water flux values decreased to 90% of their initial values. The value of the slope for the equation of a straight line emanating from the percent weight gained axis will be equal to the initial value of dy/dt evaluated at t=0, with the y intercept c defining the linear swelling time, with $(dy/dt)_0 = 0.665$ and the y intercept=0, which yields y=0.665t+0.359. In order to determine when the value of the cumulative water uptake is 90% below the initial rate, the following expression is solved for t:

$$0.9 = \frac{at^2 + bt + c}{bt + c} = \left(\frac{\Delta W}{w}\right)_{0.9} \qquad (22)$$

$$\frac{-0.00106 \ t^2 + 0.665 \ t + 0.359}{0.665 \ t + 0.359} = 0.9, \text{ and} \qquad (23)$$

solving for t, $$-0.00106t^2 + 0.0065t + 0.0359 = 0 \qquad (24)$$

$$t = \frac{-0.0665 \pm [(0.0665)^2 - 4(-0.00106)(0.0359)]^{\frac{1}{2}}}{2(-0.00106)}$$

t=62 min and the weight gain is $-0.00106(62)^2 + (0.665)(62) + 0.359 = 38$ μl, with the initial sample weight=100 mg, thus $(\Delta w/w)_{0.9} \times 100 = 38\%$. The results are presented in FIG. 8 for a graphical representation of the values. Other methods available for studying the hydrogel solution interface include rheologic analysis, viscometric analysis, ellipsometry, contact angle measurements, electrokinetic determinations, infrared spectroscopy, optical microscopy, interface morphology and microscopic examination of an operative device.

The expression active agent as used herein, includes any beneficial agent, or beneficial compound, that can be delivered from the device to produce a beneficial and useful result. The agent can be insoluble to very soluble in the exterior fluid that enters the device and it can be mixed with an osmotically effective compound and an osmopolymer. The term active agent includes algicide, antioxidant, air purifier, biocide, bactericide, catalyst, chemical reactant, disinfectant, fungicide, fermentation agent, fertility inhibitor, fertility promoter, germicide, herbicide, insecticide, microorganism attenuator, pesticide, plant growth promoter, plant growth inhibitor, preserative, rodenticide, sterilization agent, sex sterilant, and the like.

In the specification and the accompanying claims, the term beneficial agent also includes drugs. The term drugs includes any physiologically or pharmacologically active substance that produces a local or systemic effect, in animals, including warm blooded mammals, humans and primates; avians; household, sport and farm animals; laboratory animals; fishes; reptiles and zoo animals. The term physiologically, as used herein, denotes the administration of a drug to produce generally normal levels and functions. The term pharmacologically denotes generally variations in response to amount of drug administered to the host. See *Stedman's Medical Dictionary*, 1966, published by Williams and Wilkins, Baltimore, MD. The phrase drug formulation as used herein means the drug is in the compartment mixed with an osmotic solute and/or an osmopolymer and, if applicable, and with a binder and lubricant. The active drug that can be delivered includes inorganic and organic compounds. The term drug includes, for example, muscle relaxants, anti-parkinson agents, analgesics, anti-inflammatory agents, local anesthetics, muscle contractants, anti-microbials, anti-malarials, hormonal agents, contraceptives, sympathomimetics, diuretics, anti-parasitics, neoplastics, hypoglycemics, ophthalmics, electrolytes and diagnostic agents.

Exemplary drugs that are very soluble in water and can be delivered by the devices of this invention include prochlorperazine edisylate, ferrous sulfate, aminocaproic acid, potassium chloride, mecamylamine hydrochloride, procainamide hydrochloride, amphetamine sulfate, benzphetamine hydrochloride, isoproternol sulfate, methamphetamine hydrochloride, phenmetrazine hydrochloride, bethanechol chloride, methacholine chloride, pilocarpine hydrochloride, atropine sulfate, methascopolamine bromide, atropine sulfate, isopropamide iodide, tridihexethyl chloride, phenformin hydrochloride, methylphenidate hydrochloride, oxprenolol hydrochloride, metoprolol tartrate, cimetidine hydrochloride, theophylline cholinate, cephalexin hydrochloride, and the like.

Exemplary drugs that are poorly soluble in water and that can be delivered by the devices of this invention include diphenidol, prochlorperazine maleate, phenoxybenzamine. thiethylperazine maleate, anisindone, diphenadione erythrityl tetranitrate, dizoxin, isofurophate, reserpine, acetazolamide, methazolamide, bendroflumethiazide, chlorpropamide, tolazamide, clormadinone acetate, phenaglycodol, allopurinol, aluminum aspirin, methotrexate, acetyl sulfisoxazole, errthromycin, progestins, esterogenic progestational, corticosteroids, hydrocortisone, hydrocorticosterone acetate, cortisone acetate, triamcinolone, methyltesterone, 17β-estradiol, ethinyl estradiol, ethinyl estradiol 3-methyl ether, pednisolone, 17β-hydroxyprogesterone acetate, 19-nor-progesterone, norgestrel, norethindone, norethiderone, progesterone, norgesterone, norethynodrel, and the like.

Examples of other drugs that can be delivered by the osmotic device include aspirin, indomethacin, naproxen, fenoprofen, sulidac, diclofenac, indoprofen, nitroglycerin, propranolol, metoprolol, valproate, oxprenolol, timolol, atenolol, alprenolol, cimetidine, clonidine, imipramine, levodopa, chloropromazine, reserpine, methyldopa, dihydroxyphenylalanine, pivaloyloxyethyl, ester of α-methyldopa hydrochloride, theophylline, calcium gluconate, ketoprofen, ibuprofen, cephalexin, erythromycin, zomepirac, ferrous lactate, vincamine, diazepam, phenoxybenzamine. The beneficial drugs are known to the art in *Pharmaceutical Sciences,* 1979, 14th Ed., edited by Remington, published by Mack Publishing Co., Easton, PA; *The Drug, The Nurse, The Patient, Including Current Drug Handbook,* 1974–1976, by Falconer, et al., published by Saunder Company, Philadelphia, PA; and *Medicinal Chemistry,* 3rd Ed., Vol. 1 and 2, by Burger, published by Wiley-Interscience, New York.

The drug can be in various forms, such as uncharged molecules, molecular complexes, pharmacologically acceptable salts such as hydrochloride, hydrobromide, sulfate, laurylate, palmitate, phosphate, nitrite, borate, acetate, maleate, tartrate, oleate and salicylate. For acidic drugs, salts of metals, amines or organic cations; for example, quaternary ammonium can be used. Derivatives of drugs such as ester, ethers and amides can be used. Also, a drug that is water insoluble can be used in a form that is a water soluble derivative thereof to serve as a solute, and on its release from the device, is converted by enzymes, hydrolyzed by body pH or other metabolic processes to the original biologically active form. The agent, including drug, can be present in the compartment with a binder, dispersant, wetting agent, suspending agent, lubricant and dye. Representative of these include suspending agents such as acacia, agar, calcium carrageenan, alginic acid, algin, agarose powder, collagen, colloidal magnesium silicate, pectin, gelatin and the like; binders like polyvinyl pyrrolidone, lubricants such as magnesium stearate; wetting agents such as fatty amines, fatty quaternary ammonium salts, and the like. The phrase drug formulation indicates the drug is present in the compartment accompanied by an osmagnet, osmopolymer, a binder, and the like. The amount of beneficial agent in a device generally is about from 0.05 ng to 5 g or more, with individual devices containing, for example, 25 ng, 1 mg, 5 mg, 125 mg, 250 mg, 500 mg, 750 mg, 1.5 g, and the like. The devices can be administered one, twice or thrice daily.

The solubility of a beneficial agent in the fluid can be determined by known techniques. One method consists of preparing a saturated solution comprising the fluid plus the agent as ascertained by analyzing the amount of agent present in a definite quantity of the fluid. A sample apparatus for this purpose consists of a test tube of medium size fastened upright in a water bath maintained at constant temperature and pressure, in which the fluid and agent are placed and stirred by a rotating glass spiral. After a given period of stirring, a weight of the fluid is analyzed and the stirring continued an additional period of time. If the analysis shows no increase of dissolved agent after successive periods of stirring, in the presence of excess solid agent in the fluid, the solution is saturated and the results are taken as the solubility of the product in the fluid. If the agent is soluble, an added osmotically effective compound optionally may be not needed; if the agent has limited solubility in the fluid, then an osmotically effective compound can be incorporated into the device. Numerous other methods are available for the determination of the solubility of an agent in a fluid. Typical methods used for the measurement of solubility are chemical and electrical conductivity. Details of various methods for determining solubilities are described in *United States Public Health Service Bulletin,* No. 67 of the Hygienic Laboratory; *Encyclopedia of Science and Technology,* 1971, Vol. 12, pp 542 to 556, published by McGraw-Hill, Inc.; and *Encyclopedia Dictionary of Physics,* 1962, Vol. 6, pp 547 to 557, published in Pergamon Press, Inc.

The osmotic device of the invention is manufactured by standard techniques. For example, in one embodiment the beneficial agent is mixed with an osmagent and osmopolymer, and pressed into a solid possessing dimensions that correspond to the internal dimensions of the compartment adjacent to the passageway; or the beneficial agent and other formulation forming ingredients and a solvent are mixed into a solid or a semisolid by conventional methods such as ballmilling, calendering, stirring or rollmilling, and then pressed into a preselected shape. Next, a layer of a composition comprising an osmagent and an osmopolymer is laced in contact with the layer of beneficial agent formulation, and the two layers surrounded with a semipermeable wall. The layering of the beneficial agent composition and the osmagent/osmopolymer can be accomplished by conventional two-layer tablet press techniques. The wall can be applied by molding, spraying, or dipping the pressed shapes into wall-forming materials. Another and presently preferred technique that can be used for applying the wall is the air suspension coating procedure. This procedure consists in suspending and tumbling the pressed compositions in a current of air and a wall forming composition until the wall surrounds and coats the two pressed compositions. The procedure is repeated with a different lamina forming composition to form a laminated wall. The air suspension procedure is described in U.S. Pat. No. 2,799,241; *J. Am. Pharm. Assoc.,* 1979, Vol. 48, pp 451 to 459; and, ibid, 1960, Vol. 49, pp 82 to 84. Other standard manufacturing procedures are described in *Modern Plastics Encyclopedia,* 1969, Vol. 46, pp 62 to 70; and in *Pharmaceutical Sciences,* by Remington, 1970, 14th Ed., pp 1626 to 1978, published by Mack Publishing Co., Easton, PA.

Exemplary solvents suitable for manufacturing the laminates and laminae include inert inorganic and organic solvents that do not adversely harm the materials and the final laminated wall. The solvents broadly include members selected from the group consisting of aqueous solvents, alcohols, ketones, esters, ethers, aliphatic hydrocarbons, halogenated solvents, cycloaliphatics, aromatics, heterocyclic solvents, and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, chloroform, nitroethane, nitropropane, tetrachloroethane, ethyl ether, isopropyl ether, cyclohexane, cyclo-octane, benzene, toluene, naphtha, 1,4-dioxane, tetrahydrofuran, diglyme, water and mixtures thereof, such as acetone and water, acetone and methanol, acetone and ethyl alcohol, methylene dichloride and methanol, and ethylene dichloride and methanol.

DETAILED DESCRIPTION OF EXAMPLES

The following examples are merely illustrative of the present invention, and they should not be considered as limiting the scope of the invention in any way, as these examples and other equivalents thereof will become apparent to those versed in the art in the light of the present disclosure, the drawings and the accompanying claims.

EXAMPLE 1

Figure 9:
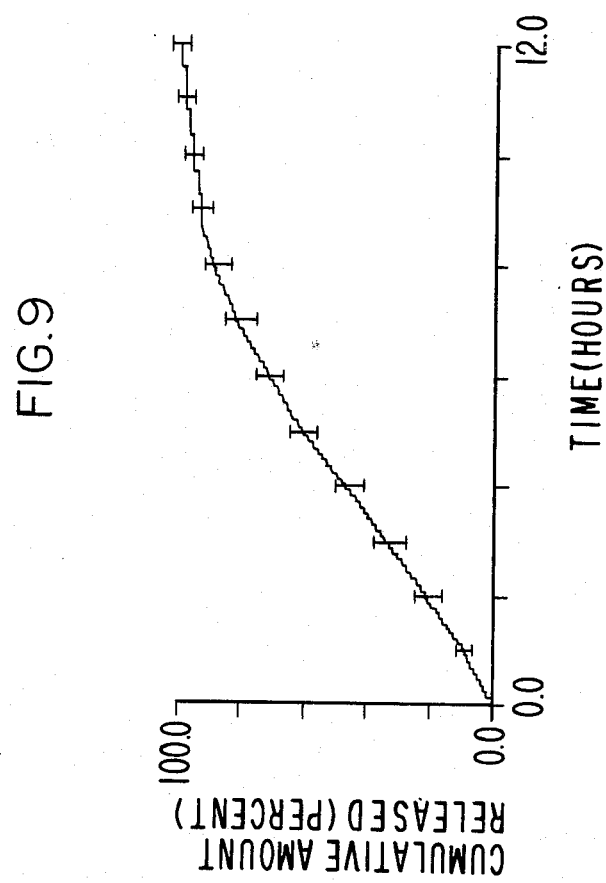
FIG. 9 depicts the cumulative amount of drug released from a device comprising an osmopolymer having two different molecular weights.

An osmotic, therapeutic device for the delivering of the drug sodium diclofenac for uses as an anti-inflammatory is prepared by first pressing in a Manesty press an osmotic drug composition containing 75 mg of sodium diclofenac, 300 mg of sorbitol, 30 mg of sodium bicarbonate, 26 mg of pectin, 10 mg of polyvinyl pyrrolidone, and 5 mg of stearic acid, and pressing the composition in a cavity to a solid layer. Next, the cavity is charged with a second and greater force generating composition comprising 122 mg of pectin having a molecular weight of 90,000 to 130,000, 32 mg of mannitol, 20 mg of polyvinyl pyrrolidone, and 2 mg of magnesium stearate and pressed to form a second layer in contacting relation with the first layer. The second layer has a density of 1.28 g/cm$^3$ and a hardness score of greater than 12 kP. Next, the two layer core is surrounded with a semipermeable wall comprised by coating 85 g of cellulose acetate having an acetyl content of 39.8%, and 15 g of polyethylene glycol 4000, 3 wt/wt percent solid in a wall forming solvent comprising 1,960 ml of methylene chloride and 819 ml of methanol. The coated device is dried for 72 hrs. at 50° C., and then a 0.26 mm diameter passageway is laser drilled through the wall. The semipermeable wall is 0.1 mm thick, the device has an area of 3.3 cm$^2$, and it has an average rate of drug release of 5.6 mg per hour over a 12 hour period. The cumulative amount released is illustrated in FIG. 9. The small vertical bars represent the minimum and maximum drug release for five systems measured at that time.

EXAMPLE 1A

The procedure of Example 1 is followed for providing an osmotic device wherein the compartment contained a blend of osmopolymers. The compartment contained a first composition weighing 312 mg and consists of 48% sodium diclofenac drug, 38% poly(ethylene oxide)osmopolymer having a molecular weight of 200,000, 10% poly(ethylene glycol)osmopolymer having a molecular weight of 20,000, 2% sodium chloride, and 2% magnesium stearate; and, a second composition weighing 150 mg and consisting of 93% poly(ethylene oxide) having a molecular weight of 5,000,000, 5% sodium chloride, and 2% magnesium stearate.

EXAMPLE 2

Figure 10:
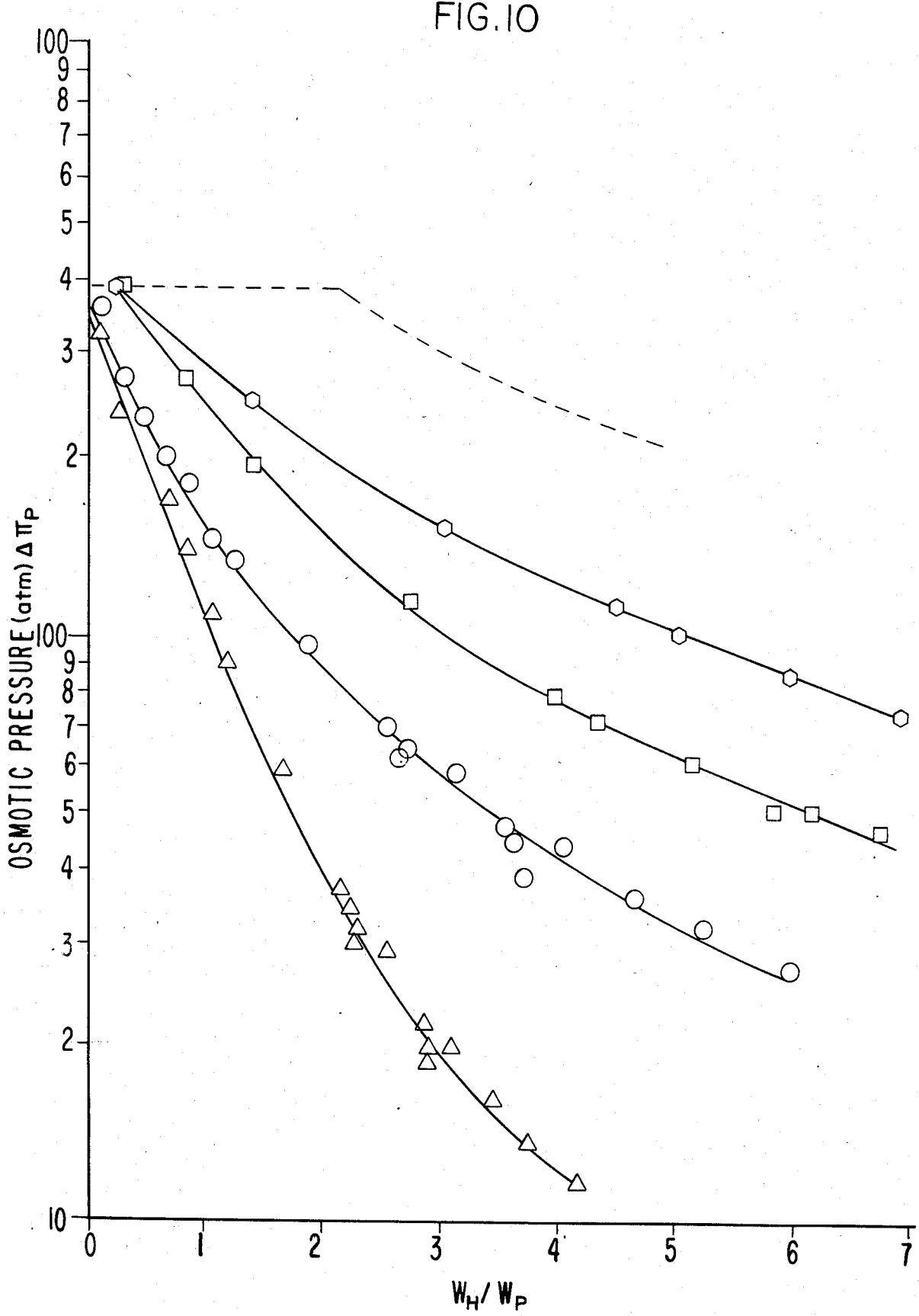
FIG. 10 depicts the osmotic pressure curves for a number of osmagent and a number of osmopolymer/osmagent compositions.

In this example, the increase in osmotic pressure for a number of compositions comprising an osmagent and as osmopolymer are made for demonstrating the operative advantage provided by the invention. The measurements are made by measuring the amount of water imbibed across the semipermeable wall of a bag containing an osmagent, or an osmopolymer, or a composition comprising an osmagent and an osmopolymer. The semipermeable wall of the bag is formed of cellulose acetate having an acetyl content of 39.8% The measurements are made by weighing the dry ingredients of the semipermeable bag, followed by weighing the blotted semipermeable bag, after the bag is in a water bath at 37° C. for various lengths of time. The increase in weight is due to water imbibition across the semipermeable wall caused by the osmotic pressure gradient across the wall. The osmotic pressure curves are illustrated in FIG. 10. In FIG. 10 the curved line with the triangles represents the osmotic pressure for poly(ethylene)oxide having a molecular weight of 5,000,000; the curved line with the circles represents the osmotic pressure for a composition comprising poly(ethylene)oxide having a molecular weight of 5,000,000 and sodium chloride with the ingredients present in the composition in the ratio of 9.5 parts osmopolymer to 0.5 parts osmagent; the curved line with squares represents a composition comprising the same osmopolymer and osmagent in the ratio of 9 parts osmopolymer to one part osmagent; the curved lines with hexagon represents the same composition comprising the osmopolymer and osmagent in the ratio of 8 parts to 2 parts; and, the dashed lines represent the osmagent sodium chloride. The mathematical calculations are made using the formula $dw/dt = A(K\pi)/h$, wherein $dw/dt$ is the rate of water imbibition over time, $\pi$ is the osmotic pressure, A is the area of the semipermeable wall, h is the semipermeable wall thickness, and K is the permeability coefficient. Also, in FIG. 10, $W_H/W_p$ is the amount of water imbibed divided by the weight of osmopolymer plus osmagent.

EXAMPLE 3

An osmotic therapeutic device for dispensing sodium diclofenac is prepared by screening through a 40 mesh screen a composition comprising 49% of sodium diclofenac, 44% poly(ethylene)oxide having a molecular weight of 100,000, 2% sodium chloride and 3% hydroxypropylmethylcellulose, and then blending the screened composition with an alcohol solvent used in the ratio of 75 ml of solvent to 100 g of granulation. The wet granulation is screened through a 16 mesh screen, dried at room temperature for 48 hours under vacuum, passed through a 16 mesh screen, and blended with 2% 80 mesh screen magnesium stearate. The composition is compressed as described above.

Figure 11:
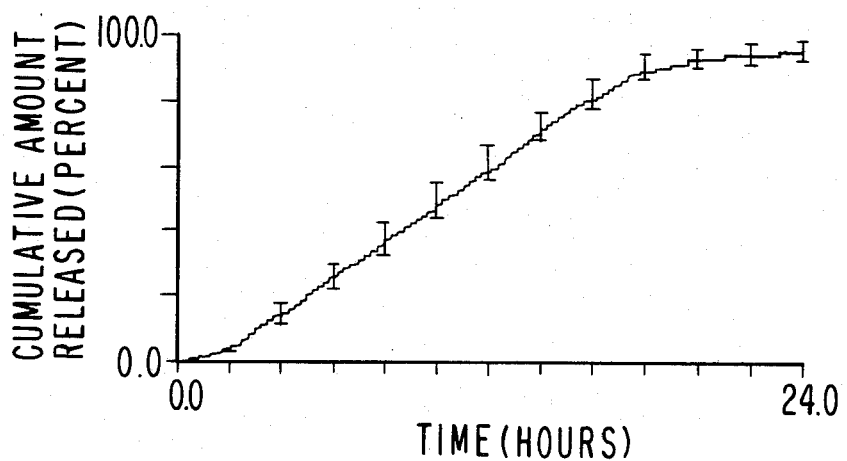
FIG. 11 depicts the cumulative release profile for an osmotic system using two different osmopolymers.
Figure 12:
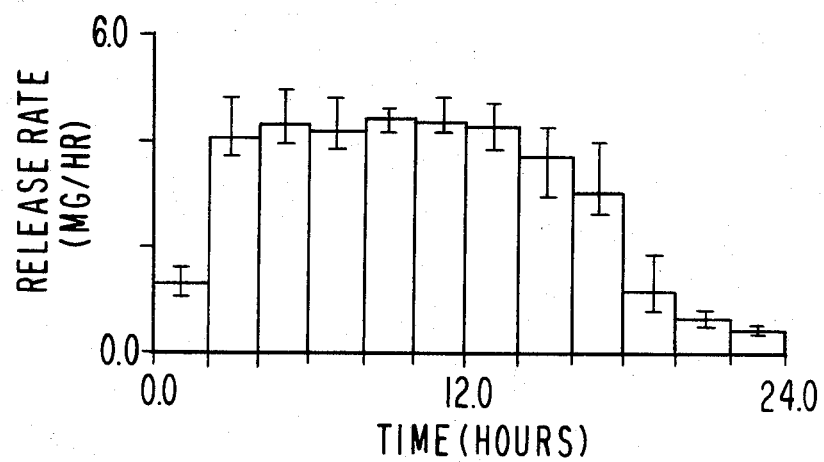
FIG. 12 depicts the release rate per hour for an osmotic system different from FIG. 9 containing an osmopolymer having two different molecular weights.

Next a composition comprising 73.9% of pectin having a molecular weight of 90,000 to 130,000, 5.8% microcrystalline cellulose, 5.8% polyvinyl pyrrolidone, 14.3% sodium chloride and 2% sucrose is passed through a 40 mesh screen, blended with an organic solvent in the ratio of 100 ml of solvent to 100 g of granulation of 25 minutes, passed through a 16 mesh screen, dried for 48 hours at room temperature under vacuum, again passed through a 16 mesh screen, blended with 2% magnesium stearate, and then compressed onto the compressed layer described in the above paragraph. The dual layered drug core is coated by dipping in a wall forming composition comprising 80% cellulose acetate having an acetyl content of 39.8%, 10% polyethylene glycol 4000, and 10% hydroxypropylmethylcellulose. A passageway is drilled through the wall communicating with the drug containing composition. The passageway diameter is 0.38 mm. The cumulative release profile for the device is depicted in FIG. 11. FIG. 12 depicts the release rate in mg per hour for the osmotic device.

EXAMPLE 4

The procedure of Example 3 is repeated with all conditions as described except that the osmopolymer in the drug composition is polyoxyethylene polyoxypropylene block copolymer having a molecular weight of about 12,500.

EXAMPLE 5

Figure 13:
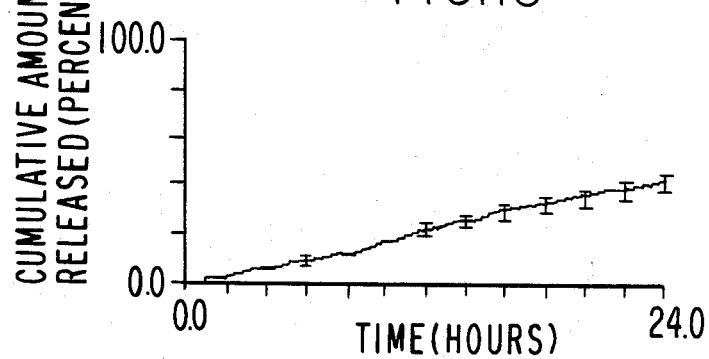
FIG. 13 depicts the cumulative amount released from a single composition device comprising only one layer.

An osmotic device is made by following the above procedures. The device of this example comprises a single composition comprising 50% of sodium diclofenac, 46% of poly(ethylene)oxide having a molecular weight of 100,000, 2% sodium chloride and 2% magnesium stearate. The device has a semipermeable wall comprising 90% cellulose acetate comprising 39.8% acetyl, and 10% polyethylene glycol 4000. The cumulative amount released for this device comprising the single composition is 40% of the device comprising two compositions. The cumulative amount released is illustrated in FIG. 13.

EXAMPLE 6

Figure 14:
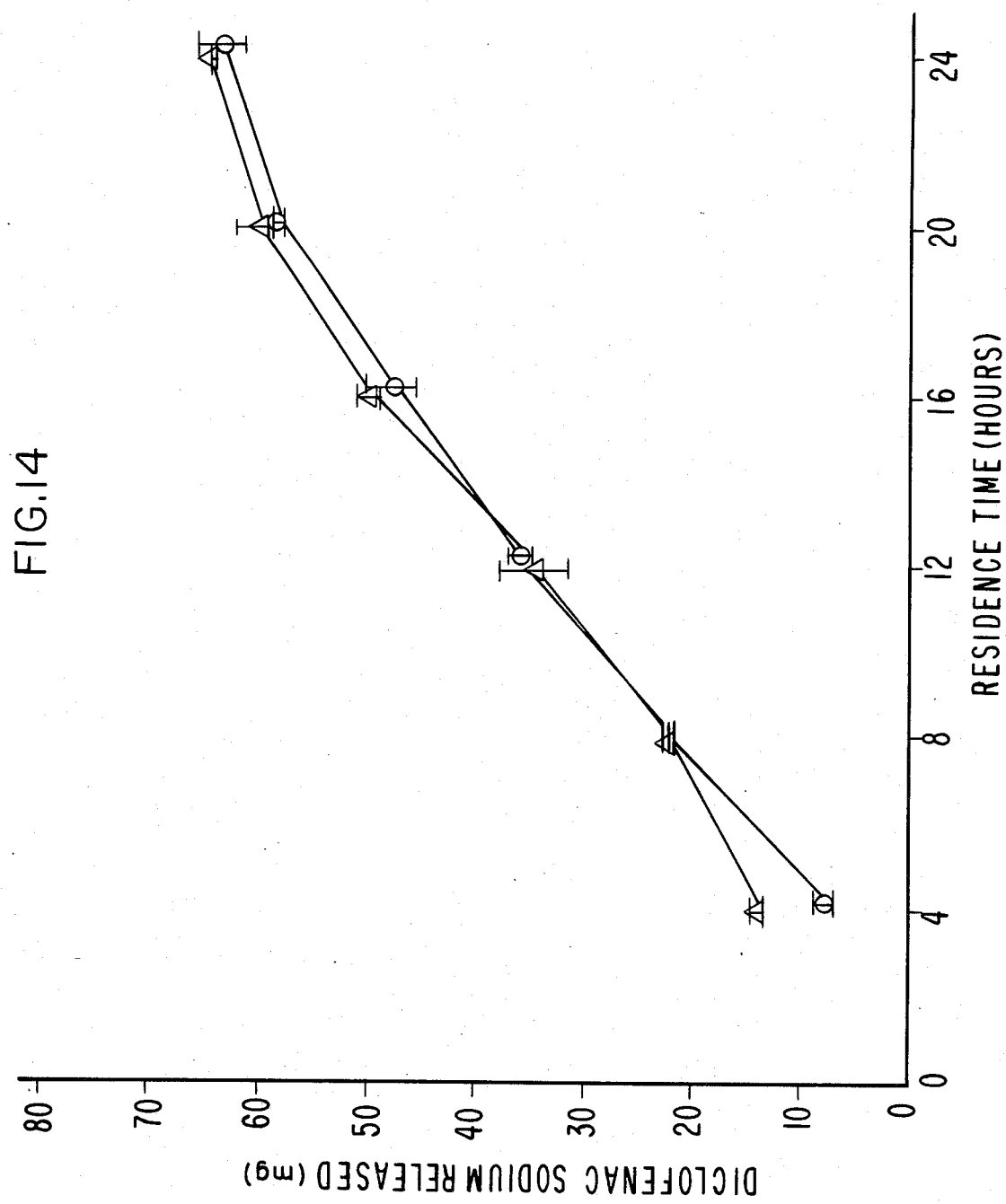
FIG. 14 illustrates the in vivo and in vitro cumulative release for one drug delivered by the osmotic device.

The in vivo and in vitro mean cumulative releases of diclofenac sodium from an osmotic device comprising a first osmotic composition comprising 75 mg of diclofenac sodium, 67 mg of poly(ethylene)oxide having a molecular weight of 100,000, 3.0 mg of sodium chloride, 4.5 mg of hydroxypropylmethylcellulose and 3.0 mg of magnesium stearate; a second osmotic composition distant from the releasing passageway comprising 51 mg of poly(theylene)oxide having a molecular weight of 5,000,000, 22.5 mg of sodium chloride, and 1.5 mg of magnesium stearate; and, surrounded by a semipermeable wall comprising 90% cellulose acetate having an acetyl content of 39.8% and 10% polyethylene glycol 4000 was measured in vivo and in vitro in laboratory dogs. The amounts of drug released at various times in vivo were determined by administering a series of devices to the animal and measuring the amount released from the corresponding device at the appropriate residence time. The results are depicted in FIG. 14, wherein the circles with the bars are the in vitro means cumulative releases and the triangles with the bars are the in vivo means cumulative releases.

EXAMPLE 7

The procedure of Example 10 is followed for making an osmotic therapeutic delivery system comprising: a first or drug composition weighing 638 mg and consisting of 96% cephalexin hydrochloride, 2% Povidone (polyvinyl pyrrolidone) and 2% magnesium stearate; a second, or osmotic deriving composition weighing 200 mg and consisting of 68.5% poly(ethylene oxide) having a molecular weight of $5 \times 10^6$, 29.4% sodium chloride, and 2% magnesium stearate; a semipermeable wall weighing 55.8 mg consisting of 80% cellulose acetate having an acetyl content of 39.8%, 10% polyethylene glycol 4000, and 10% hydroxypropylmethylcellulose; and an osmotic orifice having a diameter of 0.039 mm. The device has an average rate of release of about 54 mg per hour over a period of 9 hours.

The novel osmotic system of this invention used dual means for the attainment of precise release rate of drugs that are difficult to deliver in the environment of use, while simultaneously maintaining the integrity and the character of the system. The novel osmotic system of this invention unexpectedly and unobviously achieves controlled delivery while using at least two molecularly or structurally different polymers that exhibit different osmotic pressure gradients across a semipermeable wall, exhibit different rates of fluid imbibition through the semipermeable wall, exhibit different rates of expansion in the presence of fluid imbibed into the osmotic system, and exhibit different physical and chemical kinetics while in operation acting as a integrated unit for dispensing a beneficial agent at meaningful rates and at useful amounts from the osmotic system. While there has been described and pointed out features and advantages of the invention as applied to the presently preferred embodiments, those skilled in the dispensing art will appreciate that various modifications, changes, additions, and omissions in the system illustrated and described can be made without departing from the spirit of the invention.

We claim:

1. An osmotic device for the delivery at a controlled rate a beneficial agent to an environment of use, the osmotic device comprising:
   (a) a wall comprising in at least a part a semipermeable composition permeable to the passage of an exterior fluid present in the environment of use and substantially impermeable to the passage of a beneficial agent, the wall surrounding and forming:
   (b) a compartment;
   (c) a first composition in the compartment, said first composition comprising a beneficial agent, an osmagent that exhibits an osmotic pressure gradient across the wall against an external fluid, and an osmopolymer that exhibits an osmotic pressure gradient across the wall against an external fluid;
   (d) a second composition in the compartment, said second composition comprising an osmagent that exhibits an osmotic pressure gradient across the wall against an external fluid, and an osmopolymer that exhibits an osmotic pressure gradient across the wall against an external fluid; and,
   (e) at least one passageway in the wall communicating with the first composition and the exterior of the device for delivering the beneficial agent through the passageway from the device.

2. The osmotic device for the delivery at a controlled rate the beneficial agent according to claim 1, wherein the semipermeable composition is a member selected from the group consisting of cellulose acylate, cellulose diacylate, cellulose triacylate, cellulose acetate, cellulose diacetate and cellulose triacetate.

3. The osmotic device for the delivery at a controlled rate the beneficial agent according to claim 1, wherein the beneficial agent is a member selected from the group consisting essentially of algicide, germicide, herbicide, fungicide, insecticide and pesticide.

4. The osmotic device for the delivery at a controlled rate the beneficial agent according to claim 1, wherein the first composition is in the compartment as a layer, and the second composition is in the compartment as a layer.

5. The osmotic device for the delivery at a controlled rate the beneficial agent according to claim 1, wherein the first composition imbibes external fluid through the wall into the compartment, and the second composition imbibes external fluid through the wall into the compartment.

6. The osmotic device for the delivery at a controlled rate the beneficial agent according to claim 1, wherein the osmopolymer comprising the second composition has a molecular weight greater than the molecular weight of the osmopolymer comprising the first composition.

7. An osmotic device for the controlled delivery of a beneficial drug to a biological environment of use, comprising:
(a) a shaped wall permeable in at least a part to the passage of an exterior fluid present in the environment of use, and substantially impermeable to the passage of drug, the wall surrounding and forming:
(b) a compartment comprising: (1) a composition comprising a dosage amount of a drug, an osmotically effective compound that exhibits an osmotic pressure gradient across the wall against an external fluid, and a polymer that exhibits an osmotic pressure gradient across the wall against an external fluid, and (2) a composition comprising an osmotically effective compound that exhibits an osmotic pressure gradient across the wall against an external fluid, and a polymer that exhibits an osmotic pressure gradient across the wall against an external fluid; and,
(c) at least one passageway in the wall communicating with the exterior of the device and the composition comprising the drug for delivering a therapeutically effective amount of drug from the device at a controlled rate over a prolonged period of time.

8. The osmotic device for the controlled delivery of the beneficial drug to the biological environment of use according to claim 7, wherein the device when in operation in the environment of use, the osmotically effective compound present in composition (1) comprising the drug imbibes fluid through the wall into the compartment and the polymer present in said composition (1) imbibes fluid through the wall into the compartment for osmotically delivering the drug from the osmotic device.

9. The osmotic device for the controlled delivery of the beneficial drug to the biological environment of use according to claim 7, wherein the device when in operation in the environment of use, composition (2) comprising the osmotically effective compound and the polymer imbibes fluid through the wall into the compartment.

10. The osmotic device for the controlled delivery of the beneficial drug to the biological environment of use according to claim 7, wherein the shaped wall is formed of a semipermeable material, selected from the group consisting of cellulose acylate, cellulose diacylate, and cellulose triacylate.

11. The osmotic device for the controlled delivery of the beneficial drug to the biological environment of use according to claim 7, wherein the shaped wall is a laminate comprising a semipermeable lamina and a microporous lamina.

12. The osmotic device for the controlled delivery of the beneficial drug according to claim 7, wherein the device when in operation in the environment of use, (1) the composition comprising drug, osmotically effective compound and polymer imbibes fluid into the compartment and forms a formulation containing drug, compound and polymer, and (2) the composition comprising osmotically effective compound and polymer imbibes fluid into the compartment and forms in situ a formulation containing compound and polymer, whereby through the combined operations of (1) and (2) the formulation containing drug is delivered through the passageway from the compartment to the exterior of the osmotic device over time.

13. The osmotic device for the controlled delivery of the beneficial drug according to claim 7, wherein the polymer comprising composition (1) is water soluble.

14. The osmotic device for the controlled delivery of the beneficial drug according to claim 7, wherein the polymer comprising composition (1) is cross linked.

15. The osmotic device for the controlled delivery of the beneficial drug according to claim 7, wherein the polymer comprising composition (2) is water soluble.

16. The osmotic device for the controlled delivery of the beneficial drug according to claim 7, wherein the polymer comprising composition (2) is cross linked.

17. An osmotic device for the controlled delivery of a beneficial drug formulation to a biological environment of use, comprising:
(a) a shaped wall permeable in at least a part to the passage of an exterior biological fluid and substantially impermeable to the passage of drug formulation, which wall surrounds and forms:
(b) a compartment comprising: (1) a drug formulation, which formulation comprises a drug that is insoluble to very soluble in the biological fluid, an osmotically effective solute that is soluble in the exterior fluid and exhibits an osmotic pressure gradient across the wall against the fluid and a polymer that imbibes fluid and absorbs fluid that enters the compartment; and (2) a delivery formulation, which formulation comprises an osmotically effective solute that is soluble in the exterior fluid and exhibits an osmotic pressure gradient across the wall against the fluid and a polymer that imbibes fluid and absorbs fluid that enters the compartment; and,
(c) at least one passageway in the wall connecting the exterior of the device with the drug formulation for delivering the drug formulation from the device to the environment at a controlled rate over a prolonged period of time.

18. The osmotic device for the delivery of the beneficial drug formulation according to claim 7, wherein the biological environment of use is a human.

19. The osmotic device for the delivery of the beneficial drug formulation according to claim 7, wherein the biological environment of use is the gastrointestinal tract, and the device is shaped and adapted for oral admittance therein.

20. A composition of matter useful for forming a drug delivery system, the composition comprising in combination: (1) a first composition comprising a drug, an osmagent and an osmopolymer; and, (2) a second composition in laminar arrangement with the first composition (1), which second composition (2) comprises an osmagent and an osmopolymer, and wherein compositions (1) and (2) exhibit an osmotic pressure gradient across a semipermeable polymeric film against fluid selected from the group consisting essentially of aqueous and biological fluids.

21. The osmotic device for the delivery at a controlled rate the beneficial agent to the environment of use according to claim 1, wherein the passageway is formed in the environment of use.

22. The osmotic device for the delivery at a controlled rate the beneficial agent to an environment of use according to claim 1, wherein the wall comprises in at least a part a microporous composition comprising a pore former that is removed during the operation of the device providing at least one passageway.

23. The osmotic device for the delivery of a beneficial drug to a biological environment of use according to claim 7, wherein the passageway is formed in the environment of use.

24. The osmotic device for the controlled delivery of a beneficial drug to a biological environment of use according to claim 7, wherein the wall comprises in at least a part a microporous composition comprising a pore former that is removed during operation of the device.

25. The osmotic device for the controlled delivery of a beneficial drug to a biological environment of use according to claim 7, wherein the wall comprises in at least a part a microporous composition comprising the pore former sorbitol that is removed from the wall during operation of the device.

26. An osmotic device for the controlled delivery of a beneficial drug formulation to a biological environment of use according to claim 17, wherein the passageway in the wall is formed in the environment of use.

27. An osmotic device for the controlled delivery of a beneficial drug formulation to a biological environment of use according to claim 17, wherein the wall comprises in at least a part a microporous composition comprising a pore former that is a member selected from the group consisting of sucrose, glucose, fructose, mannitol, mannose, galactose, aldohexose, altrose, talose, sorbitol, and lactose that is removed from the wall in the environment of use providing a passageway in the wall.

* * * * *